(12) United States Patent
Gent

(10) Patent No.: US 7,964,162 B2
(45) Date of Patent: Jun. 21, 2011

(54) APPARATUS FOR HANDLING PIPET TIPS

(75) Inventor: Richard Gent, Cleveland, OH (US)

(73) Assignee: JVR Scientific LLC, South Euclid, OH (US)

( * ) Notice: Subject to any disclaimer, the term of this patent is extended or adjusted under 35 U.S.C. 154(b) by 179 days.

(21) Appl. No.: 12/204,362

(22) Filed: Sep. 4, 2008

(65) Prior Publication Data

US 2009/0092521 A1    Apr. 9, 2009

Related U.S. Application Data

(60) Provisional application No. 60/969,789, filed on Sep. 4, 2007.

(51) Int. Cl.
*B01L 3/02* (2006.01)
(52) U.S. Cl. ....................................................... 422/526
(58) Field of Classification Search .................. 422/102, 422/526
See application file for complete search history.

(56) References Cited

U.S. PATENT DOCUMENTS

| | | | | |
|---|---|---|---|---|
| 5,441,702 | A * | 8/1995 | Lemieux et al. | 422/100 |
| 5,882,603 | A * | 3/1999 | Taggart | 422/104 |
| 6,007,779 | A * | 12/1999 | Lemieux et al. | 422/100 |
| 6,098,802 | A * | 8/2000 | Asa et al. | 206/443 |
| 7,527,769 | B2 * | 5/2009 | Bunch et al. | 422/102 |
| 2003/0152494 | A1 * | 8/2003 | Moritz et al. | 422/104 |
| 2005/0150808 | A1 * | 7/2005 | Sarna et al. | 206/562 |

* cited by examiner

*Primary Examiner* — Bobby Ramdhanie
(74) *Attorney, Agent, or Firm* — Tarolli, Sundheim, Covell & Tummino LLP

(57) ABSTRACT

A pipet tip handling apparatus comprises a deep well plate that has a plurality of wells. Each of a first plurality of pipet tips has a head portion and a shank portion. A first tray is seated on the deep well plate and has openings for receiving the first pipet tips. The shank portions of the first pipet tips extend through the openings in the first tray and into the wells of the deep well plate. Each of a second plurality of pipet tips has a head portion and a shank portion. A second tray includes openings for receiving the second pipet tips. The shank portions of the second pipet tips extend through the openings of the second tray and into the head portions of the first pipet tips. The head portions of the first pipet tips support the second tray.

8 Claims, 5 Drawing Sheets

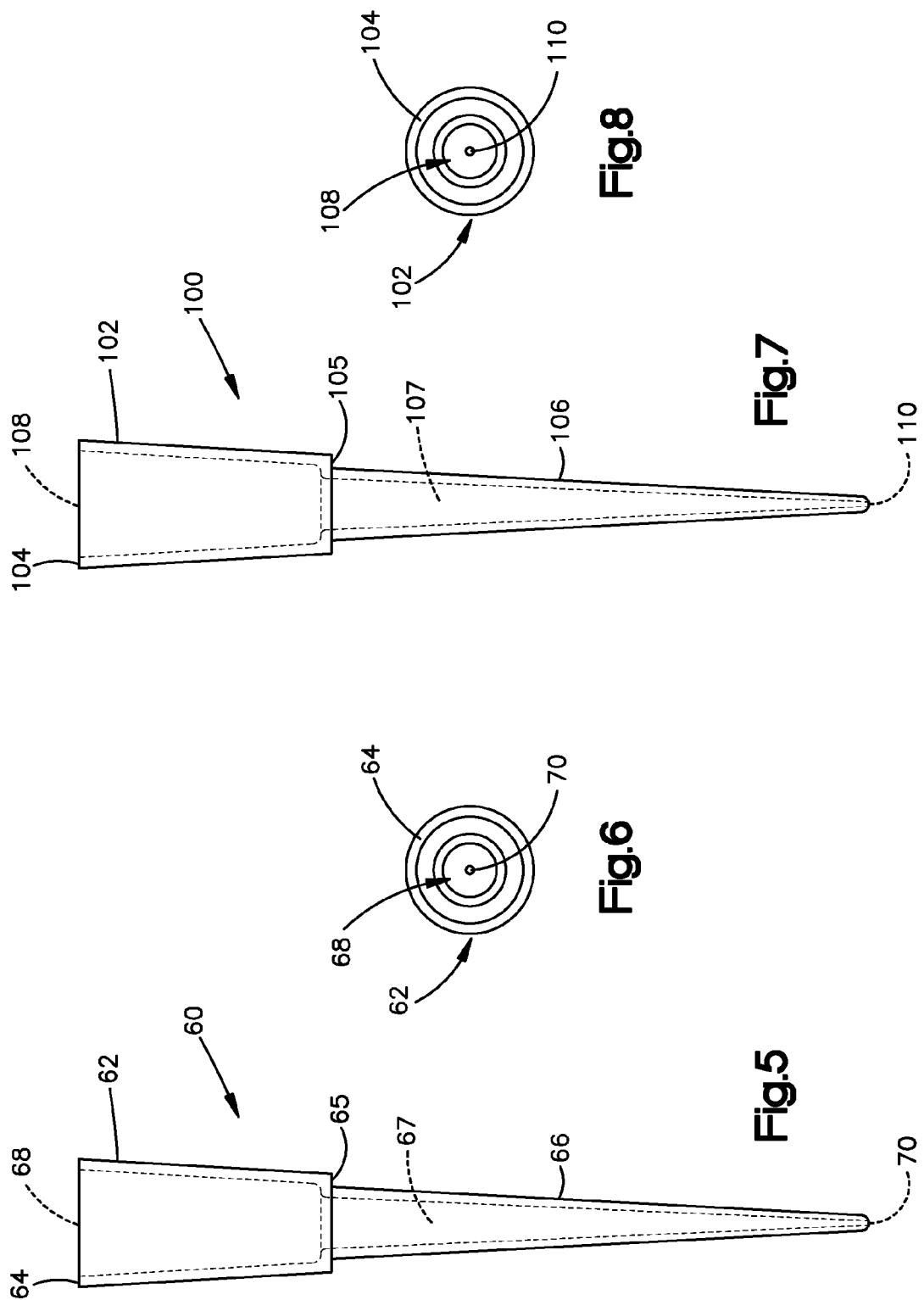

APPARATUS FOR HANDLING PIPET TIPS

RELATED APPLICATION

This application claims priority from U.S. Provisional Application No. 60/969,789, filed Sep. 4, 2007, the subject matter of which is incorporated herein by reference.

TECHNICAL FIELD

The present invention is directed to handling goods and, in particular, is directed to an apparatus for handling and storing pipet tips.

BACKGROUND OF THE INVENTION

Many products on the market are sold loaded upon regularly-sized platforms. For example, pipette tips used for sample testing in laboratories are typically loaded into pipette tip flats so that the user need not handle the pipette tips individually. By using platform loading, goods can be efficiently stored and transported in large quantities, as the platforms can be stacked and/or packaged one atop the other.

In many applications, it is desirable to utilize a device that facilitates dispensing of platforms from a stack. For example, hand loading of pipette tip flats onto pipette tip racks is generally difficult and inefficient, as the pipette tip flat must be steadily maintained in parallel and aligned with the pipette tip rack for the pipette tips extending through the flat to register with and fit into the rack. Further, in applications where contamination of the goods loaded onto the platforms is a concern or where the goods are dangerous if handled by human operators, utilizing a device for unloading the platforms removes the risks of contamination and/or injury posed by human handling of the platforms.

While current devices offer various advantages over the manual handling of pipette tip flats, there exists a continuing need for a reusable dispensing device, which can dispense units of platform loaded goods and can be simply and reliably operated by an automated system processing the units of platform loaded goods.

SUMMARY OF THE INVENTION

In accordance with the present invention, a pipet tip handling apparatus comprises a deep well plate that has a plurality of wells. Each of a first plurality of pipet tips has a head portion and a shank portion. A first tray is seated on the deep well plate and has openings for receiving the first pipet tips. The shank portions of the first pipet tips extend through the openings in the first tray and into the wells of the deep well plate. Each of a second plurality of pipet tips has a head portion and a shank portion. A second tray includes openings for receiving the second pipet tips. The shank portions of the second pipet tips extend through the openings of the second tray and into the head portions of the first pipet tips. The head portions of the first pipet tips support the second tray.

In another aspect of the invention, each well of the deep well plate can correspond with an individual volume for receiving one of the first pipet tips.

In another example, the first plurality of pipet tips can comprise 96 first pipet tips and the deep well plate can have 96 individual volumes for receiving the shank portions of the first pipet tips.

In another example, the first tray can engage only the deep well plate and the first pipet tips and/or the second tray can engage only the first pipet tips and the second pipet tips.

In another example, the head portions of the first pipet tips can have a predetermined height for allowing a robot to readily grasp the first pipet tips.

In another example, the first tray can have a lip for seating the first tray on the deep well plate.

The present invention also relates to an apparatus comprising a deep well plate that includes a rectangular base and an array of wells. Each of the wells defines an individual volume. Each of a first plurality of pipet tips has a head portion and a shank portion. A first tray has openings for receiving the first pipet tips. The shank portions of the first pipet tips extend through the openings in the first tray and into the volumes in the deep well plate. The first tray has a lip for seating the first tray on the deep well plate. Each of a second plurality of pipet tips has a head portion and a shank portion. A second tray has openings for receiving the second pipet tips. The shank portions of the second pipet tips extend through the openings in the second tray and into the head portions of the first pipet tips. The head portions of the first pipet tips support the second tray.

The present invention also relates to an apparatus comprising a deep well plate that has a top surface and a bottom surface substantially parallel to the top surface. A plurality of openings extend from the top surface toward the bottom surface and substantially perpendicular to the top surface and the bottom surface. Each of the openings defines an individual well. Each of a first plurality of pipet tips has a head portion and a shank portion. A first tray is seated on the deep well plate and has openings for receiving the first pipet tips. The shank portions of the first pipet tips extend through the openings in the first tray and into the wells of the deep well plate. Each of a second plurality of pipet tips has a head portion and a shank portion. A second tray has openings for receiving the second pipet tips. The shank portions of the second pipet tips extend through the openings of the second tray and into the head portions of the first pipet tips. The head portions of the first pipet tips support the second tray.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIG. 5 is a side elevational view of a first pipet tip in accordance with the present invention;

FIG. 6 is a top plan view of the first pipet tip of FIG. 5;

FIG. 7 is a side elevational view of a second pipet tip in accordance with the present invention;

FIG. 8 is a top plan view of the second pipet tip of FIG. 5;

DETAILED DESCRIPTION

The present invention is directed to storing goods and, in particular, is directed to an apparatus for handling and dispensing pipet tips. The apparatus comprises a deep well plate that has a plurality of wells. Each of a first plurality of pipet tips each has a head portion and a shank portion. A first tray is seated on the deep well plate and has openings for receiving the first pipet tips. The shank portions of the first pipet tips extend through the openings in the first tray and into the wells of the deep well plate. Each of a second plurality of pipet tips has a head portion and a shank portion. A second tray includes openings for receiving the second pipet tips. The shank portions of the second pipet tips extend through the openings of the second tray and into the head portions of the first pipet tips. The head portions of the first pipet tips support the second tray.

By providing the deep well plate with wells having individual volumes, the first pipet tips are kept isolated from one another as well as the surroundings to help prevent contamination. The individual wells also stabilize the first pipet tips and are sized to prevent substantial movement of the shank portions of the first pipet tips during storage and handling.

The first tray, second tray, and any subsequent trays can be substantially identical to one another. This may also be the case for the first pipet tips, second pipet tips, etc. Such a construction allows any number of trays and corresponding pipet tips to be stacked on top of one another to meet application criterion. This construction also simplifies manufacturing by limiting tooling to the production of only a few different parts.

Alternatively, each tray may be sized differently from one another, but still constructed to allow for stacking of the trays atop the deep well plate. This may be desirable where the first pipet tips, second pipet tips, etc. are different from one another.

Figure 1:
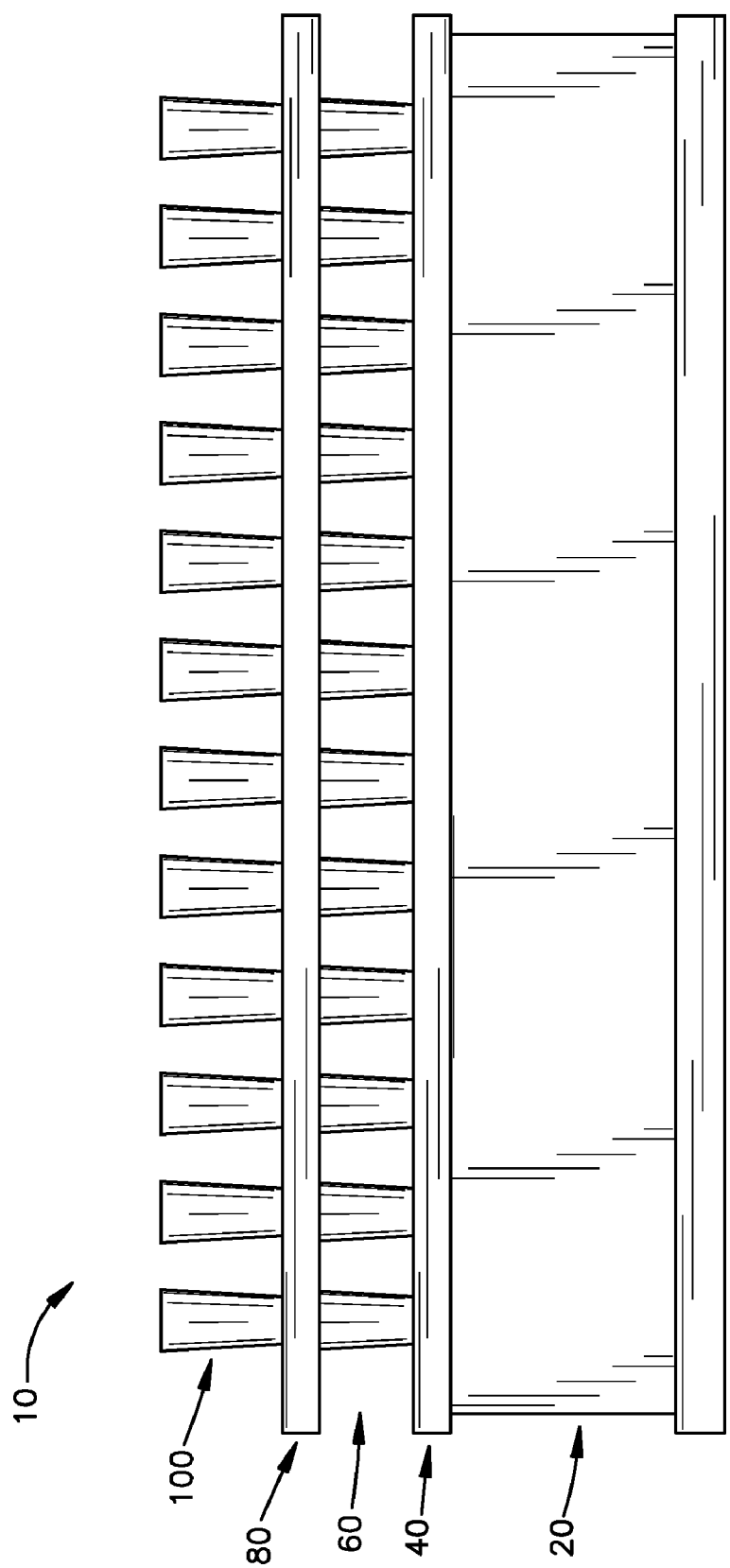
FIG. 1 is a schematic illustration of a pipet tip handling apparatus in accordance with an embodiment of the present invention.

FIG. 1 is a schematic illustration of a pipet tip handling apparatus 10 in accordance with the present invention. The apparatus 10 includes a deep well plate 20, a first tray 40, a first plurality of pipet tips 60, a second tray 80 and a second plurality of pipet tips 100.

Figure 2:
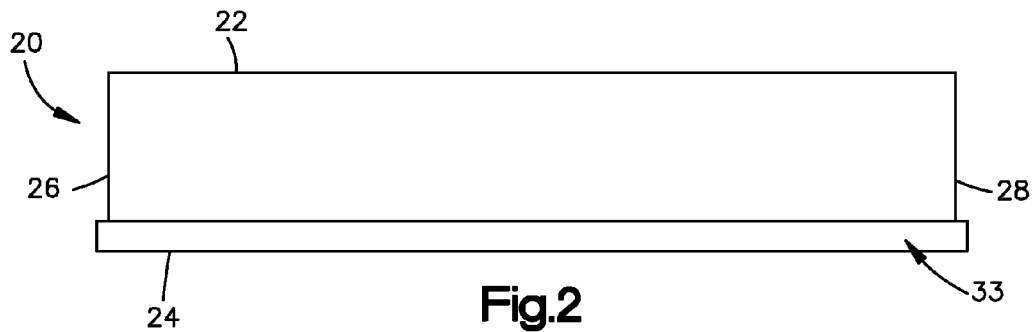
FIG. 2 is a side elevational view of a deep well plate of the apparatus of FIG. 1.
Figure 3:
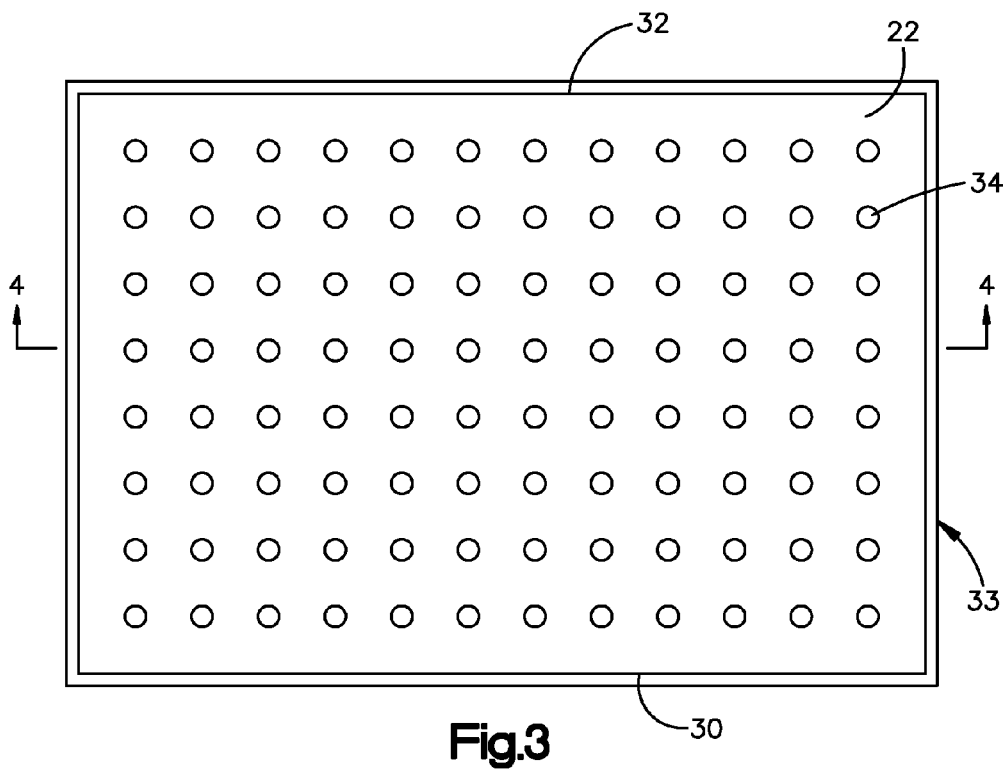
FIG. 3 is a top plan view of the deep well plate of FIG. 2.
Figure 4:
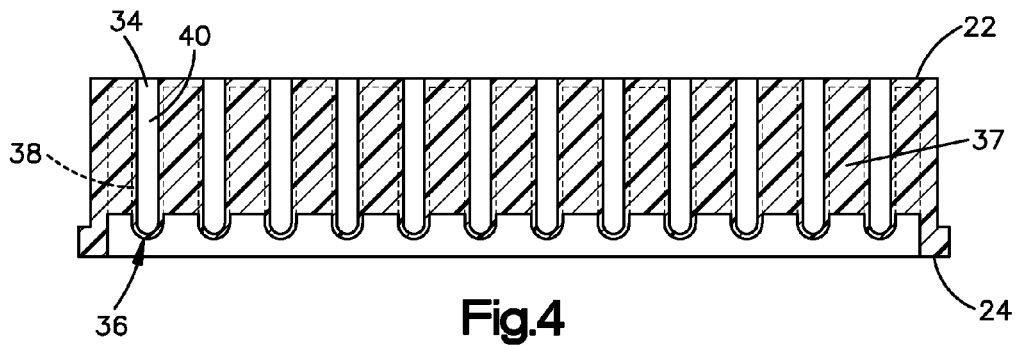
FIG. 4 is a sectional view of the deep well plate taken along line 4-4 of FIG. 3.

As shown in FIGS. 2-4, the deep well plate 20 exhibits an SBS footprint of about 127.7 mm to about 85.5 mm, which is the standard footprint on robotic decks. The deep well plate 20 has a generally rectangular or square shape and includes a top surface 22 and a substantially parallel bottom surface 24. A first side 26 and a second side 28 connect the top surface 22 to the bottom surface 24. The first and second sides 26, 28 extend generally parallel to one another. The deep well plate 20 further includes a front side 30 and a rear side 32, which connect the first side 26 to the second side 28 to form a continuous surface. The front and rear sides 30, 32 extend generally parallel to one another.

The deep well plate 20 further includes a grip pad 33 that is constructed to allow it to be easily grasped by a robotic gripping arm or other automated means. The grip pad 33 may be integrally formed with the deep well plate 20 or may separate from the deep well plate. The grip pad 33 extends laterally beyond the first and second sides 26, 28 and the front and rear sides 30, 32 such that the grip pad is concentric relative to the first and second sides and the front and rear surfaces. The grip pad 33 further extends from the bottom surface 24 toward the top surface 22 a distance predetermined to ensure that the robotic arm can securely grasp the grip pad for movement of the deep well plate 20. If the grip pad 33 is too short, the deep well plate 20 can become misaligned when gripped, causing improper placement by the robot.

The deep well plate 20 further includes a plurality of wells 36. Each of the wells 36 includes a wall 38 that extends from an opening 34 in the top surface 22 of the plate 20 toward the bottom surface 24 of the plate. Each well 36 defines an individual volume 40 that is sized to accommodate a portion of a first pipet tip 60. The wells 36 are labeled in a standard alpha-numeric pattern (not shown) to simplify sample identification.

Some or all of the wells 36 are interconnected to one another by reinforcing ribs 37. The reinforcing ribs 37 extend between the wells 36 from the first side 26 to the second side 28 and from the front side 30 to the rear side 32 (not shown) to connect the wells to all four sides of the deep well plate 20. The reinforcing ribs 37 provide additional strength and stability to the wells 36. The reinforcing ribs 37 may be integrally formed with the deep well plate 20 or, alternatively, may be separately formed and secured between and to the wells 36 in a known manner.

Although FIG. 3 illustrates an array of ninety-six wells 36 positioned in a 12×8 array about the top surface 22 of the deep well plate 20, those in the art will understand that any number of wells in any configuration, e.g., linear, arcuate, grid-like, etc., are contemplated within the spirit of the invention.

The deep well plate 20 can be formed of any material that allows the plate to be used in laboratory conditions for medical testing, chemical research, biological studies and the like. Examples of suitable materials for forming the deep well plate 20 materials include polystyrene, polytetrafluoroethylene, polycarbonate, polyvinylcholoride, high-quality virgin polypropylene and combinations thereof. The deep well plate 20 may also be resistant to a wide variety of chemicals, including phenols, chloroform, and dimethyl sulfoxids (DMSO).

As shown in FIGS. 5-6, each of the first pipet tips 60 comprises a head portion 62 and a shank portion 66. The head portion 62 is substantially frustoconical in shape and terminates at a flat surface or step 65, which extends substantially perpendicular to the length of the first pipet tip 60. Alternatively, the head portion 62 may be cylindrical. The shank portion 66 is likewise frustoconical in shape and extends from the step 65 of the head portion 62. The head portion 62 has a larger cross-section than the shank portion 66 throughout the entire length of the head portion. A passage 67 extends from an opening 68 in a top surface 64 of the head portion 62 to an opening 70 at the bottom of the shank portion 66. The passage 67 has a frustoconical shape that is concentric to the head portion 62 and the shank portion 66, although alternative shapes are contemplated.

The first pipet tips 60 can be formed from any plastic or polymer that allow it to be used in laboratories for medical testing, chemical research, biological studies, and the like. Examples of materials suitable for forming the first pipet tips 60 include polytetrafluoroethylene, polysulfone, polyethersulfone, polypropylene, polyethylene, fluoropolymers, cellulose acetate, polystyrene, polystyrene/acrylonitrile copolymer, polyvinylidene fluoride (PVDF), glass, and combinations thereof. In addition, the first pipet tips 60 can be non-conductive, conductive, sterilized, non-sterilized, or combinations thereof. The first pipet tips 60 can also be clear, colored, coated, or otherwise adapted for typical laboratory procedures.

As shown in FIGS. 7-8, each of the second pipet tips 100 comprises a head portion 102 and a shank portion 106. The head portion 102 is substantially frustoconical in shape and terminates at a flat surface or step 105, which extends substantially perpendicular to the length of the second pipet tip 100. Alternatively, the head portion 102 may be cylindrical. The shank portion 106 is likewise frustoconical in shape and extends from the step 105 of the head portion 102. The head portion 102 has a larger cross-section than the shank portion 106 throughout the entire length of the head portion. A passage 107 extends from an opening 108 in a top surface 104 of the head portion 102 to an opening 110 at the bottom of the shank portion 106. The passage 107 has a frustoconical shape that is concentric to the head portion 102 and the shank portion 106, although alternative shapes are contemplated.

The second pipet tips 100 can be formed from any plastic or polymer that allow it to be used in laboratories for medical testing, chemical research, biological studies, and the like. Examples of materials suitable for forming the second pipet tips 100 include polytetrafluoroethylene, polysulfone, polyethersulfone, polypropylene, polyethylene, fluoropolymers, cellulose acetate, polystyrene, polystyrene/acrylonitrile copolymer, polyvinylidene fluoride (PVDF), glass, and combinations thereof. In addition, the second pipet tips 100 can be non-conductive, conductive, sterilized, non-sterilized, and combinations thereof. The second pipet tips 100 can also be clear, colored, coated, or otherwise adapted for typical laboratory procedures.

Figure 9:
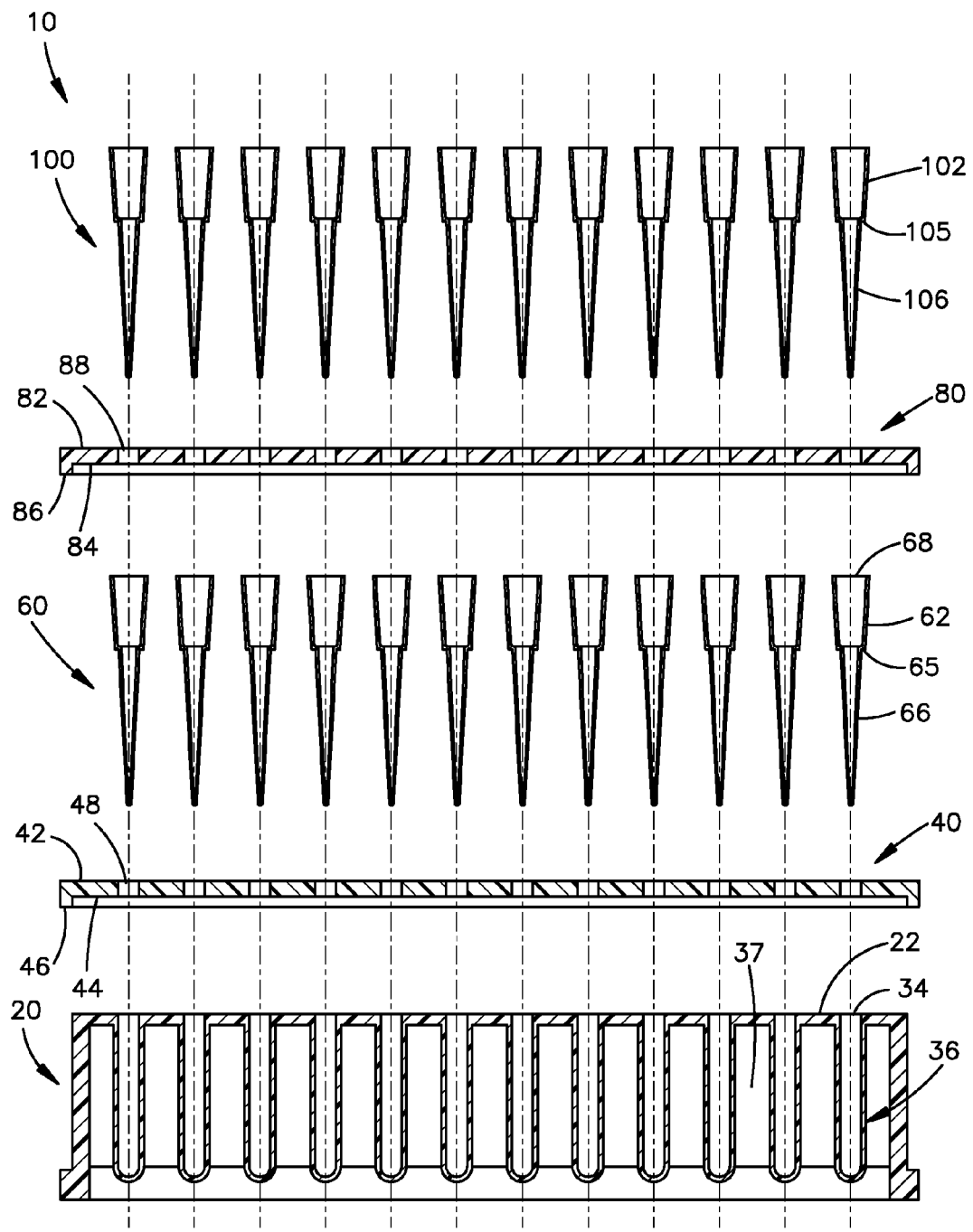
FIG. 9 is an exploded sectional view of the apparatus of FIG. 1.

The first tray 40 is generally rectangular in shape and, as shown in FIG. 9, includes a top surface 42 and a substantially parallel bottom surface 44. The bottom surface 44 of the first tray 40 has substantially the same dimensions as the top surface 22 of the deep well plate 20. The first tray 40 further includes a lip 46 for seating the first tray 40 on the deep well plate 20. The lip 46 extends from the bottom surface 44 of the first tray 40 and substantially orthogonal to the bottom surface such that the first tray can be seated on the deep well plate 20. In particular, when the first tray 40 is placed atop the deep well plate 20, the bottom surface 44 of the tray overlies the top surface 22 of the deep well plate and the lip 46 on the first tray extends adjacent, and substantially parallel to, the first and second sides 26, 28 and the front and rear sides 30, 32 of the deep well plate (see FIG. 10). This construction ensures that the first tray 40 does not move substantially relative to the deep well plate 20 when the first tray is seated on the deep well plate.

The first tray 40 further includes a plurality of openings 48 that extend from the top surface 42 to the bottom surface 44. The openings 48 are similar in size to the openings 34 in the deep well plate 20. Furthermore, the openings 48 are numbered and positioned in the same configuration as the openings 34 in the deep well plate 20. For example, the openings 48 in the first tray 40 may be constructed in the same 12×8 array as the openings 34 in the deep well plate 20.

Similar to the openings 34 and wells 36 in the deep well plate 20, the openings 48 in the first tray 40 are sized to accommodate a portion of the first pipet tips 60. In particular, the openings 48 of the first tray 40 are sized to receive the shank portions 66 of the first pipet tips 60, but the size of the steps 65 of the head portions 62 prevent the head portions from entering the openings.

The first tray 40 can be formed of any material that allows the tray to be used in laboratory conditions for medical testing, chemical research, biological studies, and the like. Examples of suitable materials for forming the first tray 40 include polyethylene, polystyrene, PTFE, PET, high-quality virgin polypropylene and combinations thereof. The first tray 40 may also be resistant to a wide variety of chemicals, including phenols, chloroform, and dimethyl sulfoxide (DMSO).

In an aspect of the present invention, the second tray 80 is identical to the first tray 40 such that the second tray can be used interchangeably with the first tray. The second tray 80 is generally rectangular in shape and includes a top surface 82 and a substantially parallel bottom surface 84. The bottom surface 44 of the second tray 80 has substantially the same dimensions as the top surface 22 of the deep well plate 20. The second tray 80 further includes a lip 86 for seating the second tray 80 on the deep well plate 20. The lip 86 extends from the bottom surface 84 of the second tray 80 and substantially orthogonal to the bottom surface such that the second tray can be seated on the deep well plate 20.

The second tray 80 further includes a plurality of openings 88 that extend from the top surface 82 to the bottom surface 84. The openings 88 is the second tray 80 are similar in size to the openings 34 in the deep well plate 20 and the openings 48 in the first tray 40. Furthermore, the number of openings 88 in the second tray 80 correspond with the number of openings 34 in the deep well plate 20 and the number of openings 48 in the first tray 40. For example, the openings 88 in the second tray 80 may be constructed in the same 12×8 array as the openings 34 in the deep well plate 20 and the openings 48 in the first tray 40.

Similar to the openings 34 and the wells 36 in the deep well plate 20, the openings 88 in the second tray 80 are sized to accommodate a portion of the second pipet tips 100. In particular, the openings 88 of the second tray 80 are sized to receive the shank portions 106 of the second pipet tips 100, but the size of the steps 105 of the head portions 102 prevent the head portions from entering the openings.

The second tray 80 can be formed of any material that allows the tray to be used for laboratory conditions. Examples of suitable materials for forming the second tray 80 include polyethylene, polystyrene, PTFE, PET, high-quality virgin polypropylene and combinations thereof. The second tray 80 may also be resistant to a wide variety of chemicals, including phenols, chloroform, and DMSO.

Figure 10:
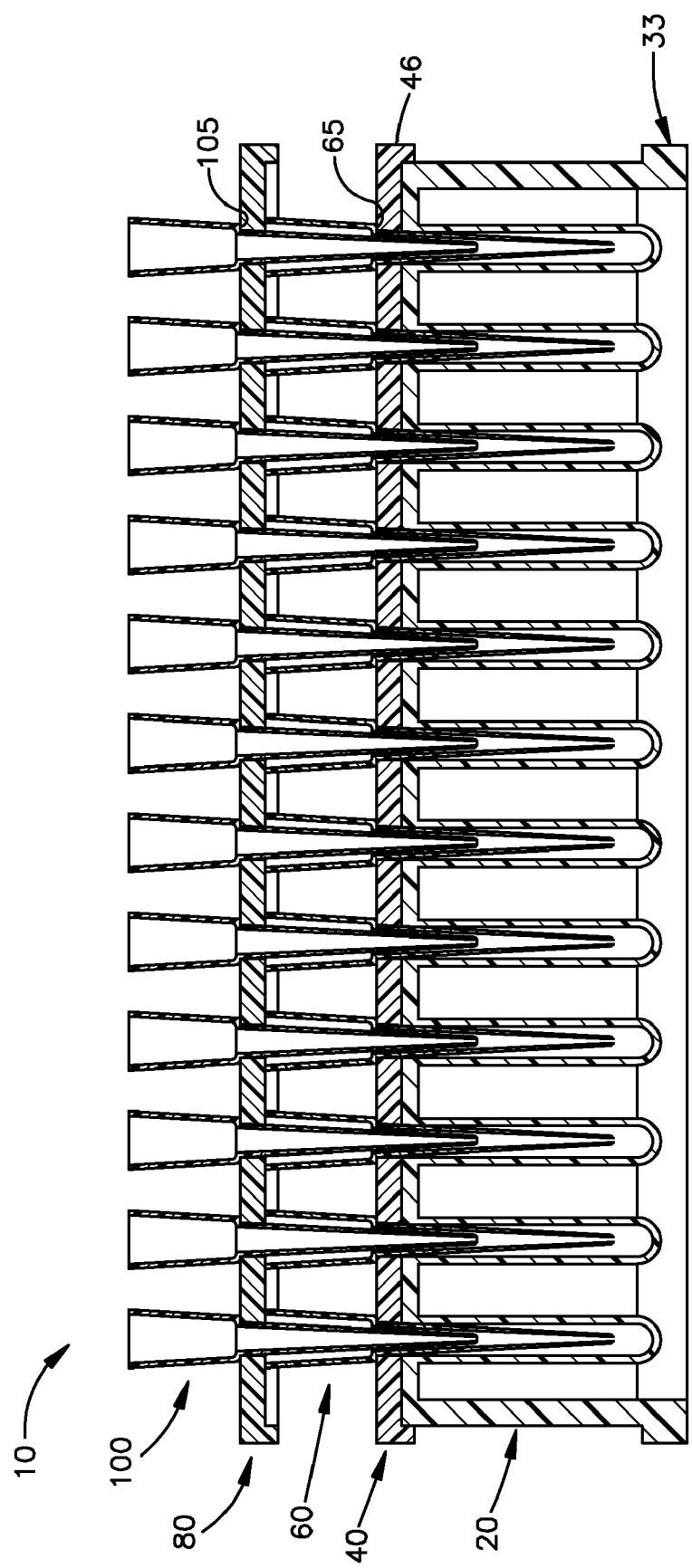
FIG. 10 is a sectional view of the apparatus of FIG. 1.

Assembly of the pipet tip handling apparatus 10 is illustrated in FIGS. 9-10. To assemble the apparatus 10, the first tray 40 is seated upon the deep well plate 20 as previously discussed such that the openings 48 in the first tray are aligned with the openings 34 and, thus, the wells 36, in the deep well plate. Since the lip 46 on the first tray 40 prevents substantial movement of the first tray relative to the deep well plate 20 when the first tray is seated upon the deep well plate, the lip 46 likewise prevents substantial movement of the openings 48 in the first tray relative to the openings 34 and the wells 36 in the deep well plate when the first tray is seated upon the deep well plate.

The first pipet tips 60 are then loaded into the first tray 40 and the deep well plate 20. To place the first pipet tips 60 in the first tray 40, the shank portions 66 of the first pipet tips are placed near, and aligned with, the openings 48 in the first tray 40. As noted, the shank portions 66 have a smaller cross sectional area than the head portions 62 of the first pipet tips 60, the openings 48 in the first tray 40, and the openings 34 in the deep well plate 20. Thus, when the first pipet tips 60 are fed through the openings 48 in the first tray 40, the shank portions 66 pass through the openings 48 in the first tray 40 and into the openings 34 in the deep well plate 20 to the wells 36. The head portions 62 of the first pipet tips 60, however, due to their size, are prevented from entering the openings 48 in the first tray 40. The steps 65 of the head portions 62, therefore, rest on the top surface 42 of the first tray. In this orientation, the first tray 40 engages only the deep well plate 20 and the first pipet tips 60.

The head portions 62 of the first pipet tips 60 are sized such that they can be readily grasped by a robot gripper arm or other automated means once the head portions become rested upon the top surface 42 of the first tray 40. This may include sizing the height and/or diameter of the head portions 62 accordingly. It is desirable to size the head portions 62 of the first pipet tips 60 in this fashion because pipet tips are frequently handled and utilized in an automated fashion due to the number of pipet tips involved.

Once the first pipet tips 60 and the first tray 40 are loaded onto the deep well plate 20, subsequent trays and pipet tips, such as the second tray 80 and the second pipet tips 100, can be loaded onto the deep well plate 20 in a vertically stacked fashion. Similar to loading the first pipet tips 60 into the first tray 40, the second pipet tips 100 are loaded into the second tray 80. This loading, however, is performed by loading the second pipet tips 100 and second tray 80 on top of the first pipet tips 60 and first tray 40. In particular, the lower surface 84 of the second tray 80 is placed on the top surfaces 64 of the head portions 62 of the first pipet tips 60 such that the openings 88 in the second tray are aligned with the openings 68 in the head portions of the first pipet tips. The head portions 62 of the first pipet tips 60 are therefore used to support the second tray 80.

The shank portions 106 of the second pipet tips 100 are then placed nearest the openings 88 in the second tray 80. As noted, the shank portions 106 have a smaller cross sectional area than the head portions 102 of the second pipet tips 100 and the openings 88 in the second tray 80. Thus, when the second pipet tips 100 are fed through the openings 88 in the second tray 80, the shank portions 106 pass through the openings 88 in the second tray 40. The head portions 102 of the second pipet tips 100, however, due to their size, are prevented from entering the openings 88 in the second tray 80. The steps 105 of the head portions 102, therefore, rest on the top surface 82 of the second tray. In this orientation, the second tray 80 engages only the first pipet tips 60 and the second pipet tips 100.

Furthermore, since the openings 88 of the second tray 80 are aligned with the openings 68 in the head portions 62 of the first pipet tips 60, the shank portions 106 of the second pipet tips 100, after extending through the openings in the second tray, extend through the openings in the head portions of the first pipet tips and into the passages 67 in the first pipet tips. In particular, the shank portions 106 of the second pipet tips 100 extend into the shank portions 66 of the first pipet tips 60. Due to the construction of the first and second pipet tips 60, 100, a tight fit is provided between the shank portions 106 of the second pipet tips and the shank portions 66 of the first pipet tips 60. This tight fit substantially prevents the second pipet tips 100 from moving relative to the first pipet tips 60 and, thus, stabilizes the second pipet tips relative to the first pipet tips. In this configuration, the first pipet tips 60 and second pipet tips 100 are stacked in a substantially concentric manner in a vertical direction relative to the deep well plate 20.

As with the head portions 62 of the first pipet tips 40, the head portions 102 of the second pipet tips 100 are sized such that they are readily graspable by a robotic arm or other automated means once the head portions become rested upon the top surface 82 of the second tray 80. By sizing the first pipet tips 40 and second pipet tips 100 in this fashion, the robotic arm is readily able to grasp and manipulate the second pipet tips 100 on the top layer of the stack. Once all the second pipet tips 100 are removed for use, the second tray 80 can be removed, thereby making the first pipet tips 60 on the layer below accessible for use.

Therefore, due to the similar construction of the first and second pipet tips 60, 100 and the first and second trays 40, 80, the present invention allows any number of trays and pipet tips to be stacked atop the deep well plate 20 for use by the robotic arm. Thus, for example, a third tray and a third plurality of pipet tips can be stacked atop, and supported by, the head portions 102 of the second pipet tips 100. As with the first and second pipet tips 60, 100, the third pipet tips will have a tight fit with the second pipet tips, thereby stabilizing the third pipet tips relative to the second pipet tips. This stacked construction can further include a fourth, fifth, etc. layer depending on the application. Accordingly, the present invention can be used to accommodate any number of applications involving any number of pipet trays and pipet tips, which are all readily graspable by the robotic arm. Furthermore, the stability provided by the grip pad 33 on the deep well plate 20 and the lip 46 on the first tray 40 allows the robotic arm to grasp and move the deep well plate and any number of pipet trays stacked thereon without misaligning the plate or causing any of the trays and/or pipet tips to fall from the stack.

From the above description of the invention, those skilled in the art will perceive improvements, changes and modifications. Such improvements, changes and modifications within the skill of the art are intended to be covered by the appended claims.

Having described the invention, the following is claimed:

1. An apparatus comprising; a deep well plate having a plurality of wells;
    wherein the plurality of wells are integral to the deep well plate, and further comprising a grip pad laterally surrounding said deep well plate; a first plurality of pipet tips, each having a head portion and a shank portion; a first tray seated on the deep well plate and having openings for receiving the first pipet tips, the shank portions of the first pipet tips extending through the openings in the first tray and into the wells of the deep well plate, wherein the first tray includes a lip extending from a bottom surface of the first tray, substantially orthogonal to the bottom surface and substantially parallel to sides of the deep well plate when the first tray is seated on the deep well plate; a second plurality of pipet tips, each having a head portion and a shank portion; and a second tray having openings for receiving the second pipet tips, wherein the shank portions of the second pipet tips extend through the openings of the second tray and into the head portions of the first pipet tips, the head portions of the first pipet tips supporting the second tray.

2. The apparatus of claim 1, wherein each well of the deep well plate corresponds with an individual volume for receiving one of the first pipet tips.

3. The apparatus of claim 2, wherein the first plurality of pipet tips comprises 96 first pipet tips, the deep well plate having 96 individual volumes for receiving the shank portions of the first pipet tips.

4. The apparatus of claim 1, wherein the first tray engages only the deep well plate and the first pipet tips.

5. The apparatus of claim 1, wherein the second tray engages only the first pipet tips and the second pipet tips.

6. The apparatus of claim 1, wherein the head portions of the first pipet tips have a predetermined height for allowing a robot to readily grasp the first pipet tips.

7. An apparatus comprising; a deep well plate comprising a rectangular base and having an array of wells, each of the wells defining an individual volume;
    wherein the plurality of wells are integral to the deep well plate, and further comprising a grip pad laterally surrounding said deep well plate; a first plurality of pipet tips, each having a head portion and a shank portion; a first tray having openings for receiving the first pipet tips, wherein the shank portions of the first pipet tips extend through the openings in the first tray and into the volumes in the deep well plate, the first tray having a lip for seating the first tray on the deep well plate, wherein the first tray includes a lip extending from a bottom surface of the first tray, substantially orthogonal to the bottom surface and substantially parallel to sides of the deep well plate when the first tray is seated on the deep well plate; a second plurality of pipet tips, each having a head portion and a shank portion; and a second tray having openings for receiving the second pipet tips, wherein the shank portions of the second pipet tips extend through the openings in the second tray and into the head portions of the first pipet tips, the head portions of the first pipet tips supporting the second tray.

8. An apparatus comprising; a deep well plate having a top surface and a bottom surface substantially parallel to the top surface, a plurality of wells including walls that extend from openings in the top surface toward the bottom surface and substantially perpendicular to the top surface and the bottom surface, each of the wells defining an individual volume; wherein the plurality of wells are integral to the deep well plate, and further comprising a grip pad laterally surrounding said deep well plate; a first plurality of pipet tips, each having a head portion and a shank portion; a first tray seated on the deep welt plate and having openings for receiving the first pipet tips, the shank portions of the first pipet tips extending through the openings in the first tray and into the volumes of the deep well plate, wherein the first tray includes a lip extending from a bottom surface of the first tray, substantially orthogonal to the bottom surface and substantially parallel to sides of the deep well plate when the first tray is seated on the deep well plate; a second plurality of pipet tips, each having a head portion and a shank portion; and a second tray having openings for receiving the second pipet tips, wherein the shank portions of the second pipet tips extend through the openings of the second tray and into the head portions of the first pipet tips, the head portions of the first pipet tips supporting the second tray.

* * * * *